United States Patent [19]

Matsumoto

[11] 4,224,326

[45] Sep. 23, 1980

[54] IMMUNOSUPPRESSIVE AGENTS

[75] Inventor: Ken Matsumoto, Indianapolis, Ind.

[73] Assignee: Eli Lilly and Company, Indianapolis, Ind.

[21] Appl. No.: 944,434

[22] Filed: Sep. 21, 1978

Related U.S. Application Data

[63] Continuation-in-part of Ser. No. 861,732, Dec. 19, 1977, abandoned.

[51] Int. Cl.² ............................................. A61U 31/505
[52] U.S. Cl. ..................................... 424/251; 544/249
[58] Field of Search ......................... 424/251; 544/249

[56] References Cited

U.S. PATENT DOCUMENTS

| | | | |
|---|---|---|---|
| 3,980,782 | 9/1976 | Paragamian et al. | 544/249 |
| 3,985,880 | 10/1976 | Paragamian et al. | 544/249 |

OTHER PUBLICATIONS

J. Med. Chem., vol. 9 (1966), pp. 599–601.
Chem. Abst. 71-112,279v.
J. Org. Chem., vol. 36, No. 11 (1971), pp. 1477–1480.
J. Heter. Chem., vol. 1, pp. 108–109, Apr. 1964.

*Primary Examiner*—Stanley J. Friedman
*Attorney, Agent, or Firm*—Kathleen R. S. Page; Arthur R. Whale

[57] ABSTRACT

The present invention is directed to certain 2-aryl-1H-perimidines as immunosuppressive agents.

15 Claims, No Drawings

IMMUNOSUPPRESSIVE AGENTS

CROSS-REFERENCE TO RELATED APPLICATION

This is a continuation-in-part of my copending application Ser. No. 861,732, filed Dec. 19, 1977, now abandoned.

SUMMARY

2-Aryl-1H-perimidine compounds of the formula

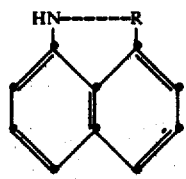

and pharmaceutically acceptable salts thereof are useful as immunosuppressive agents. In the foregoing and succeeding formulae, R represents

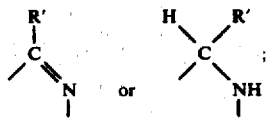

and $R^1$ represents
p-bromophenyl;
m-bromophenyl;
m- or p- $R^2$ phenyl wherein $R^2$ represents —$CF_3$, —$OCF_3$, —$SCF_3$ or —$OC_2F_5$;
p-chlorophenyl;
p-isopropylphenyl; or
a radical of the formula

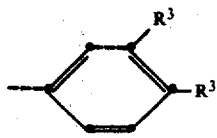

wherein each $R^3$ independently represents bromo or chloro.

The $R^1$=m or p- $R^2$ phenyl compounds are also claimed herein as novel compounds.

DETAILED DESCRIPTION

In Formula I, the carbon atom of the

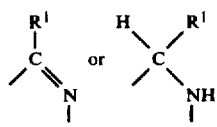

unit is always intermediate to the two nitrogen atoms, so that Formula I designates only two types of structures:

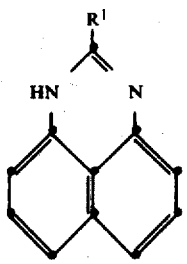

and

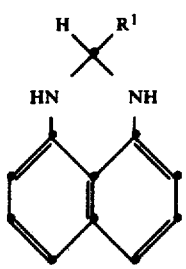

Many of the compounds serving as the present active agent are known compounds. All of the compounds are prepared in accordance with known procedures which involve the condensation of 1,8-diaminonaphthalene

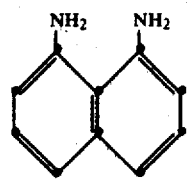

with an acyl halide of the formula $R^1COX$, to prepare compounds of Formula II; or with an aldehyde of the formula $R^1CHO$, to prepare compounds of Formula III. Attention is directed to J. Het. Chem. 1, 108 (1964), J. Org. Chem. 36 #11, 1477 (1971), and the references cited in each.

Most of the acyl halides and aldehydes which are employed as starting materials are known compounds, and all are prepared in conventional procedures. The m- and p-trifluoromethoxybenzoyl fluorides are prepared by chlorinating an alkyl m- or p-methoxybenzoate and reacting the resulting m- or p-trichloromethoxybenzoyl chloride with a mixture of $SbF_3$ and $SbCl_5$. The m- and p-trifluoromethylthiobenzoyl chlorides are prepared by reacting an alkyl m- or p-iodobenzoate with $Hg(SCF_3)_2$, hydrolyzing the resulting alkyl m- or p-trifluoromethylthiobenzoate, and converting the free acid to an acid chloride with e.g., $SOCl_2$. The m- and p-pentafluoroethoxybenzoyl chlorides are prepared as follows: m- or p-bromophenol is acylated with trifluoroacetic anhydride to yield m- or p-bromophenyl trifluoroacetate, which is reacted with $SF_4$ to obtain m- or p-pentafluoroethoxyphenyl bromide. It is converted to the corresponding acid by reaction with butyl lithium and $CO_2$, then converted to the acyl chloride with $SOCl_2$. The corresponding aldehydes, to be used in the preparation of the compounds of Formula III, are prepared from the acyl halides in conventional procedures.

The present invention is directed to a method for suppressing the immune reaction in mammals. Such suppression includes the suppression of immune response engendered whenever the mammalian body forms antibodies and reactive cells in response to the presence of foreign protein. The practical application of immunosuppressive activity is varied. A prominent application of immunosuppressive activity is in the transplanting of organs; but immunosuppressive activity can also be advantageously employed in the therapy of the various diseases known collectively as "auto-immune" diseases. Representative auto-immune diseases include auto-immune hemolytic anemia, idiopathic thrombocytopenic purpura, lupus erythematosus, lupoid hepatitis, lupus nephritis, glomerulonephritis, the nephrotic syndrome, Goodpasture's syndrome, Wegener's granulomatosis, schleroderma, Sezary's disease, psoriasis, uveitis, rheumatoid arthritis, ulcerative colitis, thyroiditis and mumps orchitis.

In implementing the present immunosuppressing method, administration can be by the oral or parenteral routes. The precise amount of active agent to be employed varies from compound to compound. However, the compounds have a high therapeutic index, so that effective, non-toxic doses, in each case, extend over a wide range. Depending upon the test system, this range, for the more active members of the series tested in small mammals, extends from <1.6 to 25 mg/kg/day. Other compounds of the series require more, such as up to 100 mg/kg/day or more, in small mammals. Given the relationship between small and large animal doses seen with other drugs—e.g., the human dose of the immunosuppressant, azathioprine is generally 1-2 mg/kg, whereas the mouse dose is approximately 50 mg/kg (see also *Cancer Chemotherapy Reports* 50:219; 1966)—the anticipated effective human dose levels would be correspondingly lower than in small mammals, such as from 0.5-10 mg/kg/day.

The present compounds are preferably administered in the form of a pharmaceutical formulation. Pharmaceutical formulations are well known in the pharmaceutical art. In making a formulation with the present active agent, the compound of choice is mixed with a carrier such as lactose, dextrose, sucrose, sorbitol, mannitol, starches, gum acacia, calcium phosphate, alginates, tragacanth, gelatin, methyl cellulose, talc, magnesium stearate, or mineral oil. The formulation can be prepared as a tablet, suspension or capsule. For parenteral use, the compounds are formulated as injectable solutions.

A preferred formulation is one in dosage unit form adapted for oral administration to obtain an immunosuppressive effect, which comprises, per dosage unit, an immunosuppressive, non-toxic amount within the range from about 10 to about 100 milligrams of the present active agent, and a pharmaceutical diluent.

The following examples illustrate the present invention.

EXAMPLE 1

PREPARATION OF
2-(p-TRIFLUOROMETHYLPHENYL)-1H-PERIMIDINE HYDROCHLORIDE

A solution of 31.64 g. (0.20 mole) of 1,8-diaminonaphthalene in 500 ml. of benzene and a solution of 20.8 g. (0.20 mole) of p-trifluoromethylbenzoyl chloride in 500 ml of benzene were added simultaneously to 500 ml. of benzene with vigorous stirring at room temperature. After stirring for approximately ½ hour the solid was collected and triturated with methanol, yielding 24.6 g. as the hydrochloride salt (35% yield), m.p. 210° C. (dec), mass spectrum m/e 312.

Analysis, calc. for $C_{18}H_{12}N_2ClF_3$: C, 61.99; H, 3.47; N, 8.03; Cl, 10.17; F, 16.34. Found: C, 61.75; H, 3.59; N, 8.02; Cl, 10.45; F, 16.70.

EXAMPLE 2

PREPARATION OF
2-(m-TRIFLUOROMETHYLPHENYL)-1H-PERIMIDINE HYDROCHLORIDE 1,8-Diaminonaphthalene (15.82 g.; 0.10 mole) and m-trifluoromethylbenzoyl chloride (20.8 g.; 0.10 mole) were reacted in the same procedures as reported in Example 1, yielding 33.3 g. (95.4% yield) of 2-(m-trifluoromethylphenyl)-1H-perimidine hydrochloride, m.p. 280° C. (dec), mass spectrum m/e 312.

Analysis, calc. for $C_{18}H_{12}N_2ClF_3$: C, 61.99; H, 3.47; N, 8.03. Found: C, 61.68; H, 3.59; N, 8.13.

EXAMPLE 3

PREPARATION OF
2-(p-TRIFLUOROMETHOXYPHENYL)-1H-PERIMIDINE HYDROFLUORIDE 1,8-Diaminonaphthalene (1.52 grams; 0.0096 mole) was dissolved in 25 ml. of toluene, then decanted. p-Trifluoromethoxybenzoyl fluoride (2.0 grams; 0.0096 mole) was dissolved in 25 ml. of toluene. Both solutions were added simultaneously to 25 ml. of toluene. After the reaction mixture had been stirred for approximately 4 hours, TLC indicated that the reaction was complete.

The reaction mixture was filtered and the product, a yellow solid, was dried, 2.72 grams (81.4% yield), m.p. 195° C. (dec), mass spectrum m/e 328 with smaller peaks at 361 indicating trace amounts of —$OCFCl_2$.

Analysis, calc. for $C_{18}H_{12}F_4N_2O$: C, 62.07; H, 3.47; N, 8.04; F, 21.82. Found: C, 61.81; H, 3.58; N, 8.13; F, 21.59.

EXAMPLE 4

PREPARATION OF
2-(p-TRIFLUOROMETHYLTHIOPHENYL)-1H-PERIMIDINE HYDROCHLORIDE 1,8-Diaminonaphthalene (14.59 grams; 0.092 mole) and p-trifluoromethylthiobenzoyl chloride (22.2 grams; 0.092 mole) were reacted in the procedures of Example 3, yielding 31.86 grams of product (91.0% yield), m.p., 276° C. (dec.), mass spectrum m/e 344. It was suspended in 500 ml. of toluene and stirred for approximately 2 hours, then separated by filtration, 30.6 grams (87.4% yield), m.p., 270° C. (dec.). It was then resuspended in 750 ml. of toluene, boiled for 2 hours, and separated by filtration, 29.7 grams (84.8% yield).

Analysis, calc. for $C_{18}H_{12}ClF_3N_2S$: C, 56.77; H, 3.18; N, 7.36. Found: C, 56.57; H, 3.37; N, 7.40.

EXAMPLE 5

PREPARATION OF
2-(p-PENTAFLUOROETHOXYPHENYL)-1H-PERIMIDINE HYDROCHLORIDE 1,8-Diaminonaphthalene (1.04 grams; 0.00656 mole) and p-pentafluoroethoxybenzoyl chloride (1.8 grams; 0.00656 mole) were reacted in the procedures of Example 3, yielding 2.25 grams of product (82.7% yield), m.p., 240° C. (dec.), mass spectrum m/e 378.

Analysis, calc. for $C_{19}H_{12}ClF_5N_2O$: C, 55.02; H, 2.92; N, 6.75; F, 22.90. Found: C, 54.82; H, 3.15; N, 6.49; F, 23.20.

EXAMPLES 6-19

MOUSE HEMAGGLUTININ ASSAY, ORAL ADMINISTRATION

Groups of five 20-gram, male, random-bred, Swiss mice received intravenous injections of $5 \times 10^7$ sheep red blood cells. The cells for these injections were prepared from lamb's blood (collected in Alsever's solution) by washing three times with 0.85 percent saline and resuspending in 0.85 percent saline. Nine daily doses of each compound to be tested, solubilized in polyethylene glycol 400, were administered orally in 0.1 ml. doses, commencing three days prior to red blood cell injection. Several dose levels of each compound were employed, at 2-fold increments. A control group of mice, receiving a red blood cell injection and nine daily doses of vehicle instead of drug, was included. Six days after the antigen injections, the mice were bled by cardiac puncture and the sera from each 5-mouse group pooled. The serum pools, following complement inactivation, were assayed for hemagglutinin content by standard procedures, utilizing a mixture of serial 2-fold saline dilutions of the test sera with 0.5 percent sheep red blood cell suspensions in plastic depression trays. Following incubation of the trays for 3 hours at 37° C., the hemagglutination patterns were graded. A 4-fold (75 percent) or greater antibody reduction (in the test serum as compared with the control serum) was considered significant. The results were expressed as the minimum effective dose ("MED")—the lowest drug dose producing 75 percent or greater antibody reduction.

The results of testing the perimidine compounds of this invention for their ability to reduce antibody production are summarized in Table I. Azathioprine (IMURAN), which is used for clinical immunosuppression, has an MED of 100 mg./kg. ×9 by this test.

TABLE I

| Compound | MED mg/kg × 9 PO |
|---|---|
| 2-(p-bromophenyl)-1H-perimidine | 25 |
| 2,3-dihydro-2-(p-bromophenyl)-1H-perimidine | 25 |
| 2-(p-chlorophenyl)-1H-perimidine | 100 |
| 2-(p-trifluoromethyl-phenyl)-1H-perimidine hydrochloride | 6.25 |
| 2-(m-trifluoromethyl-phenyl)-1H-perimidine hydrochloride | 100 |
| 2-(p-bromophenyl)-1H-perimidine hydrochloride | 12.5 |
| 2-(m-bromophenyl)-1H-perimidine hydrochloride | 100 |
| 2-(3,4-dichlorophenyl)-1H-perimidine hydrochloride | 12.5 |
| 2-(4-bromo-3-chlorophenyl)-1H-perimidine hydrochloride | 50 |
| 2-(3-bromo-4-chlorophenyl)-1H-perimidine hydrochloride | 50 |
| 2-(3,4-dibromophenyl)-1H-perimidine hydrochloride | 50 |
| 2-(p-trifluoromethoxyphenyl)-1H-perimidine hydrofluoride | <100 |
| 2-(p-trifluoromethylthiophenyl)-1H-perimidine hydrochloride | <100 |
| 2-(p-pentafluoroethoxyphenyl)-1H-perimidine hydrochloride | 100 |

TABLE I-continued

| Compound | MED mg/kg × 9 PO |
|---|---|

EXAMPLES 20-24

INDIVIDUAL SERUM ASSAY PROCEDURE

In these tests, the procedure described above in Examples 3-13 was modified by the use of 10-mouse groups, rather than 5-mouse groups. The mice were bled as before, but the sera were titered individually rather than as a pool. Mean hemagglutinin values $(\log_2) \pm S.E.$ were calculated for each 10-mouse group and p values (by Student's t Test), in comparison with the control group, were determined. The lowest drug dose significantly ($p < 0.05$) lowering antibody titer defined the endpoint. The drugs were administered orally or subcutaneously in ten daily doses, commencing three days prior to red blood cell injection. Drugs were suspended in a vehicle composed of saline containing 0.125 percent methylcellulose and 0.2 percent nonionic emulsifying agent. Antibody (hemagglutinin) determinations were made seven days following a red blood cell injection. Typical results obtained in the individual serum assay test with representative compounds of the invention are summarized in Table II.

TABLE II

Immunosuppressive Activity of Compounds (Individual Serum Assay Procedure)

| Compound | Route | Endpoint Dose ($p < 0.05$) in mg/kg × 10 |
|---|---|---|
| 2-(p-trifluoromethyl-phenyl)-1H-perimidine hydrochloride | oral | <1.6 |
|  | subcu. | <1.6 |
| 2-(p-bromophenyl)-1H-perimidine hydrochloride | oral | 25 |
|  | subcu. | <3.1 |
| 2-(3,4-dichlorophenyl)-1H-perimidine hydrochloride | oral | <3.1 |
|  | subcu. | <3.1 |
| 2-(p-trifluoromethoxy-phenyl)-1H-perimidine hydrofluoride | oral | 12.5 |
| 2-(p-trifluoromethylthio-phenyl)-1H-perimidine hydrochloride | oral | 50 |

EXAMPLES 25-26

GRAFT-VERSUS-HOST (GVH) REACTION

In this test, parental (C57BL) mouse spleen cells are injected into mice of an $F_1$ hybrid strain (C57BL×C3H). The recipient mice do not reject the injected spleen cells, since the hybrid recognizes C57BL-related antigens from its homozygous parent as "self." The injected cells, however, mount a reaction to the recipient's tissue due to the foreign C3H-derived antigens. As a consequence, the recipient's spleen becomes enlarged. Immunosuppression prevents or reduces this enlargement. Thus, spleen weights provide a measure of the GVH reaction and its reduction under immunosuppression.

A modification of Simonsen's original procedure (*Ann. N.Y. Acad. Sci.* 73:834, 1958) was employed. Large crops of spleen cells were obtained, without the generally employed manual teasing of spleens, by using Waring blendors with the cutting blades reversed. Two six-second blending periods buffeted the spleens (batches of 25 C57BL spleens in 25-ml saline) sufficiently to free the cells from the connective tissue. The latter was removed by filtration through several thicknesses of cheesecloth. Cell suspensions prepared in this fashion were standardized, by means of Levy-Hausser chamber counts, to contain $6 \times 10^8$ nucleated cells per ml. Groups of ten 16–18 gram C57BL×C3H mice were injected intraperitoneally with 1 ml of the donor cell suspension. Treatment, by the oral or subcutaneous route in 0.2 ml, was instituted 3 days prior to cell injection and continued daily for 13 days. Control animals received only cells and vehicle. The spleens were removed and weighed 10 days following cell injection. The results were expressed as mg spleen/gram body weight.

Since the injection of syngeneic, i.e., C57BL×C3H, cells into the recipient mice produces a minor degree of splenomegaly, spleen weights of such animals were used to define 100% suppression of the GVH component in calculating percents of inhibition produced by the immunosuppressive compounds. The method of calculation is illustrated in the following example from mice treated with a reference immunosuppressive compound:

| Reference Compound Treatment | Mg Spleen/g Body Wt. ± S.E.* | Percent Inhibition** |
|---|---|---|
| 1-(6-methoxy-2-benzothiazolyl)-3-phenylurea (cf. J. Med. Chem. 12, 1016–1018 (1969)), 12.5 mg/kg × 13 (orally) | 6.86 ± 0.80*** | 74 |
| None (GVH Control) | 11.55 ± 1.01 | 0 |
| None (Syn. Control) | 5.20 ± 0.37 | 100 |
| None (Normal Control) | 4.16 ± 0.17 | — |

*Mean values from groups of 5 mice.

** $\left( \frac{\text{GVH Control} - \text{Treated}}{\text{GVH Control} - \text{Syn Control}} \right) \times = \text{Percent Inhibition}$

***p<0.01, compared with GVH control

Since in practice it was found that both syngeneic and normal controls varied only slightly from test to test, a composite value (4.8), derived from recalculating four separate syngeneic control groups (5.20±0.37, 4.99±0.39, 4.42±0.13, 4.66±0.12) as a 20-mouse group was used in the calculations. The results obtained in the graft-versus-host reaction with the compounds of the invention are summarized in Table III.

TABLE III

| Compound | Dose (mg/kg × 13) | Mg Spleen/g mouse weight (mean + S.E.) | Percent Inhibition$^a$ GVH Series |
|---|---|---|---|
| 2-(p-bromophenyl)-1H-perimidine (subcutaneous) | 50 | 4.70 ± 0.21$^b$ | 102 |
|  | 25 | 5.43 ± 0.41$^b$ | 84 |
|  | 12.5 | 5.64 ± 0.65$^c$ | 79 |
|  | 6.2 | 6.18 ± 0.39$^d$ | 66 |
|  | 3.1 | 8.08 ± 0.66 | 19 |
| (Control) | — | 8.84 ± 0.72 |  |
| 2-(p-trifluoromethylphenyl)-1H-perimidine hydrochloride (oral) | 25 | 4.75 ± 0.42$^c$ | 101 |
|  | 12.5 | 6.62 ± 1.17 | 53 |
|  | 6.2 | 5.67 ± 0.51$^e$ | 77 |
|  | 3.1 | 4.96 ± 0.31$^d$ | 96 |
|  | 1.6 | 5.66 ± 0.33$^e$ | 78 |
| (Control) | — | 8.64 ± 1.10 |  |

$^a \frac{\text{GVH Control} - \text{Treated}}{\text{GVH Control} - \text{Syn. Control}} \times =$ percent inhibition
$^b$ p <0.001
$^c$ p <0.005
$^d$ p <0.01
$^e$ p <0.05

EXAMPLE 27

ADJUVANT-INDUCED ARTHRITIS TEST IN RATS 2-(p-Trifluoromethylphenyl)-1H-perimidine hydrochloride was tested for its ability to alter hind paw swelling and bone damage resulting from adjuvant-induced edema in rats. In order to quantitate the inhibition of hind paw swelling resulting from adjuvant-induced arthritis, two phases of inflammation have been defined: (1) the primary and secondary *injected* hind paw, and (2) the secondary *uninjected* hind paw, which generally begins developing about nine days from the induction of inflammation in the injected paw. Reduction of the latter type of inflammation is an indication of immunosuppressive activity Cf. Chang, *Arth. Rheum.* 20: 1135–1141 (1977). Fenoprofen (30 mg./kg.) was included as a standard anti-inflammatory compound for comparative evaluation (Nickander et al., *Fed. Proc. Annual FASEB Mtgs.*, April, 1971, ABS #205).

Adjuvant arthritis was induced in male Lewis-Wistar rats (200–210 grams) by a single subplantar injection into the right hind paw of 0.1 ml of a 0.5% suspension of heat-killed, lyophilized *Mycobacterium tuberculosis* (Calbiochem-Perrigen-C) in mineral oil (a modification of a method reported by Winter et al., *Arth. Rheum.* 9: 394–397 (1966)). One group of 5 rats ("TB control") received only this treatment. Another group of 5 rats received no treatment (normal control.) Each compound to be tested was suspended in carboxymethylcellulose (1%) and administered by gavage to rats (groups of 5 each) in daily oral doses of 30 mg/kg., beginning on day one and continuing through the 17th day after the adjuvant injection (17 doses). Paw volumes were measured by mercury displacement using a Statham pressure transducer and digital voltmeter. Volumes of both the injected and the uninjected hind paws were measured on days 2, 4, 7, 9, 11, 14, 16 and 18. X-ray photos were taken on day 18 after the animals were sacrificed. The paw volume measurements on the uninjected paw beginning with day 9 through day 18 were as follows.

TABLE IV

| | Uninjected Paw Volume Measurements From Day 9 Through Day 18 | | | | |
|---|---|---|---|---|---|
| Treatment | Day 9 | Day 11 | Day 14 | Day 16 | Day 18 |
| (normal control) | 1.99 ± 0.063 | 2.13 ± 0.08 | 2.08 ± 0.053 | 2.15 ± .056 | 2.01 ± 0.95 |
| TB control | 1.94 ± 0.028 | 2.02 ± 0.037 | 2.69 ± 0.106 | 3.26 ± 0.202 | 3.65 ± 0.227 |
| fenoprofen | 1.97 ± 0.023 | 2.11 ± 0.07 | 2.38 ± 0.099 | 2.7 ± 0.107 | 2.67 ± 0.128 (23% inhibition)* |
| 2-(p-trifluoromethylphenyl)-1H-perimidine | 1.93 ± 0.081 | 1.95 ± 0.079 | 2.13 ± 0.148 | 2.35 ± 0.233 | 2.53 ± 0.39 (69% inhibition)* |

$$*\% \text{ Inhibition} = 1 - \frac{\text{Volume of Drug Treated} - \text{Volume of Normal Control}}{\text{Volume of TB Control} - \text{Volume of Normal Control}} \times 100$$

Gross observation of X-ray photos taken of both injected and uninjected paws indicated no bone damage in the animals treated with 2-(p-trifluoromethylphenyl)-1H-perimidine hydrochloride, whereas bone damage was very obvious in the TB control group.

I claim:

1. A method for suppressing mammalian immune response which comprises administering to a mammal in need of immune response suppression an effective amount of an active agent which is a compound of the formula

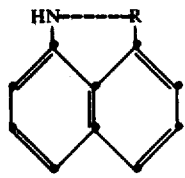

or a pharmaceutically-acceptable salt thereof, wherein R represents

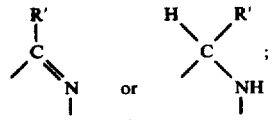

and R¹ represents
p-bromophenyl;
m-bromophenyl;
m- or p- R² phenyl wherein R² represents —CF₃, OCF₃, —SCF₃, or —OC₂F₅;
p-chlorophenyl;
p-isopropylphenyl; or
a radical of the formula

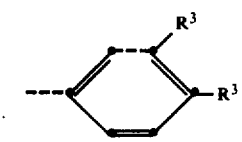

wherein each R³ independently represents bromo or chloro.

2. The method of claim 1 wherein the mammal has received an organ transplant.

3. The method of claim 2 wherein the active agent is 2-(p-bromophenyl)-1H-perimidine or a pharmaceutically acceptable salt thereof.

4. The method of claim 2 wherein the active agent is 2-(p-trifluoromethylphenyl)-1H-perimidine or a pharmaceutically acceptable salt thereof.

5. The method of claim 1 wherein the mammal is suffering an auto-immune disease.

6. The method of claim 5 wherein the auto-immune disease is lupus erythematosus.

7. The method of claim 6 wherein the active agent is 2-(p-bromophenyl)-1H-perimidine or a pharmaceutically acceptable salt thereof.

8. The method of claim 6 wherein the active agent is 2-(p-trifluoromethylphenyl)-1H-perimidine or a pharmaceutically acceptable salt thereof.

9. The method of claim 5 wherein the auto-immune disease is rheumatoid arthritis.

10. The method of claim 9 wherein the active agent is 2-(p-bromophenyl)-1H-perimidine or a pharmaceutically acceptable salt thereof.

11. The method of claim 9 wherein the active agent is 2-(p-trifluoromethylphenyl)-1H-perimidine or a pharmaceutically acceptable salt.

12. A pharmaceutical formulation in dosage unit form adapted for oral administration to obtain an immunosuppressive effect, which comprises, per dosage unit, an immunosuppressive, non-toxic amount within the range from about 10 to about 1000 milligrams of an active agent which is a compound of the formula

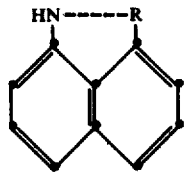

or a pharmaceutically-acceptable salt thereof, wherein R represents

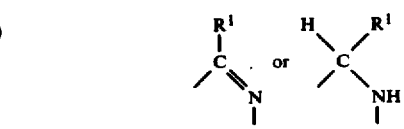

and R¹ represents
m- or p- R² phenyl wherein R² represents —CF₃, —OCF₃, —SCF₃, or —OC₂F₅;
and a pharmaceutical diluent.

13. The formulation of claim 12 in which the active agent is 2-(p-trifluoromethylphenyl)-1H-perimidine or a pharmaceutically acceptable salt thereof.

14. The formulation of claim 12 in which the active agent is 2-(p-trifluoromethoxyphenyl)-1H-perimidine or a pharmaceutically acceptable salt thereof.

15. The formulation of claim 12 in which the active agent is 2-(p-trifluoromethylthiophenyl)-1H-perimidine or a pharmaceutically acceptable salt thereof.

* * * * *